US006437093B1

(12) United States Patent
Lieberman et al.

(10) Patent No.: US 6,437,093 B1
(45) Date of Patent: Aug. 20, 2002

(54) METHODS OF TREATMENT COMPRISING ADMINISTRATION OF SUBSTANCE P

(75) Inventors: Allan D. Lieberman, Charleston, SC (US); John McMichael, Delanson, NY (US)

(73) Assignee: Milkhaus Laboratory, Inc., Deanson, NY (US)

( * ) Notice: Subject to any disclaimer, the term of this patent is extended or adjusted under 35 U.S.C. 154(b) by 0 days.

(21) Appl. No.: 09/723,699

(22) Filed: Nov. 28, 2000

(51) Int. Cl.[7] .................. A61K 38/08; A61K 38/04; C07K 7/00
(52) U.S. Cl. ................ 530/327; 530/327; 530/300; 514/2; 514/15
(58) Field of Search ................ 514/2, 15; 530/300, 530/327

(56) References Cited

U.S. PATENT DOCUMENTS

| 5,420,297 A | | 5/1995 | Matsuo et al. | |
| 5,633,232 A | | 5/1997 | Matsuo et al. | |
| 5,945,508 A | * | 8/1999 | Witten et al. | ............... 530/327 |

OTHER PUBLICATIONS

Frederickson et al., Dual Actions of Substance P on Nociception: Possible Role of Endogenous Opiods. Science 199, 1359–1362 (1978).*
Oehme et al., Substance P: Does It Produce Analgesia or Hyperalgesia? Science 208, 305–307 (1980).*
Cross et al., "Further characterisation of substance P induced histamine release from human bronchoalveolar lavage mast cells" *Inflamm Res 45, Supplement 1*:S11–S12 1996.
Henry, "Substance P and inflammatory pain: potential of substance P antagonists as analgesics", *Inflammatory Disease Therapy* pp. 75–87 (1993).
Meggs, "Rads and Ruds—The toxic induction of asthma and rhinitis", *Clinical Toxicology*, 32(5), 487–501 (1994).
Tomlinson, et al., "Neurotrophins and peripheral neuropathy", *Phil. Trans. R. Soc. Loud*, B351 455–462 (1996).

* cited by examiner

*Primary Examiner*—Karen Cochrane Carlson
*Assistant Examiner*—Chih-Min Kam
(74) *Attorney, Agent, or Firm*—Marshall, Gerstein & Borun

(57) ABSTRACT

A method for treatment of symptoms of a respiratory disease or pain in a subject comprising administering to said subject a Substance P in an amount effective to alleviate those symptoms.

11 Claims, No Drawings

METHODS OF TREATMENT COMPRISING ADMINISTRATION OF SUBSTANCE P

BACKGROUND OF THE INVENTION

Substance P is a protein naturally occurring in the body. It is a tachykinin which induces contraction of smooth muscle and appears in humans and other mammals at highest concentrations in brain, intestine, spinal ganglia.

Since the late 1970's, studies have shown that Substance P has a variety of biological activities including acting as a vasodilator, stimulates salivation, can cause increased gut permeability. Of particular interest to the present invention is the observation that Substance P can, at different concentrations, cause analgesia or hyperalgesia. Although its biological activity can be difficult to measure, its activity as a systemic signal is highly stable at ambient and refrigerated temperatures.

Substance P can act as a neurotransmitter or a hormone (particularly in the gut as a hormone). The vasodilation caused by Substance P is a result of its direct inhibitory effect on arteriolar smooth muscle. This effect is mediated by receptors. that appear specific to Substance P versus other vasodialators. Of interest to the present invention is that those receptors appear to be identical to those specific for rubeola virus. While Substance P inhibits contraction of arteriolar smooth muscle, it stimulates contraction of intestinal, bronchial and venous smooth muscle. Substance P can also cause diuresis and natriuresis in kidneys. These observations suggest that there could be more than one type of Substance P receptor.

SUMMARY OF THE INVENTION

The present invention relates to the observation that Substance P appears to be a signal for the mediation of neurogenic pain and that it would appear to be a candidate as a therapeutic agent for those types of pain which are most difficult to control, especially peripheral neuropathy.

The present invention provides methods for treatment of disease states selected from the group consisting of respiratory dysfunction and pain comprising administration of an effective amount of Substance P. The invention also provides pharmaceutical compositions for treatment of respiratory dysfunction and pain comprising an effective amount of Substance P in combination with a suitable carrier.

It is believed that Substance P may function in the treatment of pain by having a direct effect on pain receptors. Moreover, while not wishing to be bound by any particular theory of the invention, Substance P may operate in treatment of certain respiratory conditions such as Reactive Upper Airway Dysfunction (RUDS) through a mechanism of treatment of neuropathy. Specifically, RUDS has been described as a cranial nerve neuropathy involving the 10th cranical nerve (vagus). Accordingly, it may be that Substance P treats respiratory conditions such as RUDS through a mechanism which treats neuropathies associated with those diseases.

An effective amount of Substance P according to the invention is an amount which results in a reduction in the symptoms of a respiratory disease or of pain symptoms. Amounts of Substance P ranging from $10^{-7}$ to $10^{-2}$ mg are contemplated to be effective according to the invention. While preferred dosages include those ranging from $10^{-5}$ to $10^{-4}$ mg Substance P and $8 \times 10^{-5}$ mg has been found to be particulary effective when administered from one to six times daily in the form of sublingual drops, those of ordinary skill would be capable of adjusting the dosage amounts and schedule by observation of the effectiveness of treatment. Accordingly, it is contemplated that the range in dosage for the application could be several logs higher or lower than the optimum above. While the preferred route of administration is sublingual administration, it would be apparent to those of skill in the art that other routes would also be suitable for treatment according to the invention including subcutaneous administration, intramuscular, intravenous administration and the like. The invention also provides pharmaceutical compositions for treatment of respiratory conditions and pain comprising Substance P in combination with a suitable carrier such as saline or other pharmaceutically acceptable excipients.

DETAILED DESCRIPTION OF THE INVENTION

EXAMPLE 1

According to this example, a male presented with upper airway distress ho had a persistent cough triggered by exposure to volatile chemicals. His disease appeared to be initiated by chronic exposure to floor stripper which caused RUDS (Reactive Upper Airway Dysfunction). This cough was stopped almost immediately by treatment with Substance P which was administered by sublingual drop (0.05 ml/drop) at one drop per hour for three hours and then one drop four times daily. Each drop contained $8 \times 10^{-5}$ mg synthetic Substance P (Sigma) in phosphate buffered saline.

EXAMPLE 2

According to this example, an 8 year old boy presented with a repetitive, almost tic-like, exaggerated cough that was disruptive to his classmates and teacher. Several physicians were consulted without success and with no apparent cause found for the cough. Substance P was administered by sublingual administration according to the method of Example 1 and stopped the cough within minutes. Practice of the method of the invention continued to control this disorder after more than a year.

EXAMPLE 3

According to this example, a 49 year old female presented RUDS that manifested as severe hoarseness or even aphonia if exposed to volatile chemicals, and especially to fragrances. She had suffered for several years after being exposed to fragrances from several co-workers using multiple perfumes. Her airway problem was reduced only by complete avoidance of any exposure to volatile chemicals which dramatically changing her lifestyle. Sublingual administration of Substance P according to the method of Example 1 provided significant improvement and has allowed her to return to more normal living. Her RUDS continues to be controlled by taking one drop of Substance P four times daily, or more frequently if needed.

EXAMPLE 4

According to this example, a 63 year old woman presented with a history of numbness, tingling and severe pain in feet and legs eight years earlier. During the year immediately preceding her first office visit, the discomfort had spread to her hands. She had a history of familial diabetes, but she did not test diabetic. No cause of her discomfort could be determined, and the only relief she obtained was from narcotic analgesics.

The subject was treated by sublingual administration of Substance P according to the method of Example 1 and she experienced almost immediate pain relief. As a result, the subject was able to discontinue narcotics, and continues well with continued Substance P treatment.

EXAMPLE 5

According to this example, a 69 year old woman presented with severe sciatic-like pain of the hip of long duration. The subject also presented with a diagnosis of diabetes. The subject was treated by sublingual administration of Substance P according to the method of Example 1 which reduced the pain dramatically. She continues well for over two years.

EXAMPLE 6

According to this example, a 44 year old female presented with a diagnosis of chronic sciatic pain that was disabling and of several years duration. Analgesics helped reduce the pain. The subject was treated by sublingual administration of Substance P according to the method of Example 1. The first sublingual drop of Substance P instantly and dramatically "turned off" the pain. The Patient continued over several months to use daily doses of Substance P with continued control of pain.

EXAMPLE 7

According to this example, a 59 year old woman with arthritis-like pain and inflammation of the knuckles but who tested negative for rheumatoid factor. Pain was not significantly reduced by over the counter formulations or prescription drugs. The subject was treated by sublingual administration of Substance P according to the method. of Example 1. After three days of Substance P sublingual drop therapy, the patient reported "remarkable" improvement that continued after two months.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

What is claimed:

1. A method for the treatment of symptoms of neuropathic pain in a mammal comprising administering to said mammal a Substance P in an amount effective to alleviate those symptoms, the amount being a dosage of from $10^{-5}$ mg to $10^{-4}$ mg administered from one to six times daily.

2. The method of claim 1 wherein Substance P is administered by a route selected from the group consisting of sublingual administration and subcutaneous administration.

3. The method of claim 2 wherein Substance P is administered by sublingual administration.

4. The method of claim 1 wherein the mammal is human.

5. The method of claim 1 wherein the neuropathic pain involves the cranial nerves.

6. A method for the treatment of symptoms of reactive upper airway dysfunction (RUDS) in a mammal comprising administering to said mammal a Substance P in an amount effective to alleviate those symptoms.

7. The method of claim 6 wherein the mammal is a human.

8. The method of claim 6 wherein Substance P is administered by a route selected from the group consisting of sublingual administration and subcutaneous administration.

9. The method of claim 6 wherein Substance P is administered by sublingual administration.

10. The method of claim 9 wherein Substance P is administered at a dosage of from $10^{-7}$ mg to $10^{-2}$ mg one to six times daily.

11. The method of claim 9 wherein Substance P is administered at a dosage of from $10^{-5}$ mg to $10^{-4}$ mg one to six times daily.

* * * * *